(12) United States Patent
Barrett et al.

(10) Patent No.: US 9,952,127 B2
(45) Date of Patent: Apr. 24, 2018

(54) TRIPHASIC FLUID HANDLING

(71) Applicant: GenCell Biosystems Ltd., Raheen, County Limerick (IE)

(72) Inventors: Brian Barrett, Cashel (IE); Caitriona Ryan, Lahinch (IE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 141 days.

(21) Appl. No.: 14/816,838

(22) Filed: Aug. 3, 2015

(65) Prior Publication Data

US 2016/0033370 A1    Feb. 4, 2016

Related U.S. Application Data

(60) Provisional application No. 62/032,885, filed on Aug. 4, 2014.

(51) Int. Cl.
| | | |
|---|---|---|
| *G01N 1/10* | (2006.01) | |
| *G01N 1/28* | (2006.01) | |
| *B01L 3/00* | (2006.01) | |
| *B01L 3/02* | (2006.01) | |

(52) U.S. Cl.
CPC .............. *G01N 1/28* (2013.01); *B01L 3/0293* (2013.01); *B01L 3/502* (2013.01); *B01L 3/502784* (2013.01); *B01L 3/0241* (2013.01); *B01L 2200/025* (2013.01); *B01L 2200/0673* (2013.01); *B01L 2300/0838* (2013.01); *B01L 2400/0487* (2013.01)

(58) Field of Classification Search
CPC .................................... G01N 1/10; G01N 1/28
USPC .......... 422/68.1, 502, 503, 504; 436/43, 180
See application file for complete search history.

(56) References Cited

U.S. PATENT DOCUMENTS

| | | | |
|---|---|---|---|
| 8,465,707 B2* | 6/2013 | Curran ................ | B01F 13/0071 422/501 |
| 9,080,208 B2* | 7/2015 | Curran ................ | B01F 13/0071 |
| 9,194,772 B2 | 11/2015 | Lee et al. | |
| 2002/0185457 A1 | 12/2002 | Smith et al. | |
| 2003/0125590 A1* | 7/2003 | Curran ..................... | C07B 37/04 568/959 |
| 2004/0247487 A1 | 12/2004 | Commercon et al. | |
| 2006/0201390 A1* | 9/2006 | Lahann .................. | B82Y 10/00 106/401 |
| 2007/0275415 A1* | 11/2007 | Srinivasan .......... | B01F 13/0071 435/7.4 |
| 2012/0045765 A1* | 2/2012 | Curran ................ | B01F 13/0071 435/6.12 |
| 2013/0260447 A1 | 10/2013 | Link | |
| 2014/0134717 A1 | 5/2014 | Moon et al. | |
| 2014/0371107 A1* | 12/2014 | Curran ................ | B01F 13/0071 506/26 |

(Continued)

FOREIGN PATENT DOCUMENTS

| | | |
|---|---|---|
| EP | 1905513 A1 | 4/2008 |
| EP | 2538228 A2 | 12/2012 |
| EP | 2752671 A2 | 7/2014 |

(Continued)

*Primary Examiner* — Brian J. Sines
(74) *Attorney, Agent, or Firm* — Bozicevic, Field & Francis LLP; Bret E. Field

(57) ABSTRACT

Aspects of the present disclosure include methods of moving a target fluid in a triphasic fluid arrangement from a vessel into a tube and systems and devices for practicing the same.

17 Claims, 12 Drawing Sheets

(56) References Cited

U.S. PATENT DOCUMENTS

2017/0101358 A1* 4/2017 Khan .................. C07C 5/03

FOREIGN PATENT DOCUMENTS

| WO | WO 2007/024778 A2 | 3/2007 |
|----|-------------------|--------|
| WO | WO 2007/024798 A2 | 3/2007 |
| WO | WO 2007/024800 A2 | 3/2007 |
| WO | WO 2007/024914 A2 | 3/2007 |
| WO | 2012011091 A2 | 1/2012 |
| WO | 2013111016 A2 | 8/2013 |
| WO | 2014083435 A2 | 6/2014 |
| WO | 2014188281 A2 | 11/2014 |
| WO | 2014207577 A2 | 12/2014 |
| WO | 2015075560 A2 | 5/2015 |
| WO | 2015075563 A2 | 5/2015 |

* cited by examiner

TRIPHASIC FLUID HANDLING

CROSS-REFERENCE TO RELATED APPLICATIONS

Pursuant to 35 U.S.C. § 119 (e), this application claims the benefit of priority to U.S. Provisional Patent Application Ser. No. 62/032,885, filed Aug. 4, 2014, the disclosure of which application is hereby incorporated by reference herein in its entirety.

INTRODUCTION

Processing of biological samples can be advantageously done within a fluid system involving three mutually immiscible liquids. Such a system can be used to create composite liquid cells (CLCs) in which a sample fluid is isolated by an encapsulating fluid, and both of which float on top of a carrier fluid. CLCs are described in more detail in U.S. Pat. No. 8,465,707, which is hereby incorporated herein by reference in its entirety.

In many implementations, CLCs are centered around an aqueous phase which contains a sample or reagent of interest, e.g., a biological component or reagent. The aqueous phase floats on top of a carrier fluid that is immiscible with, and more dense than, the aqueous phase. Above the aqueous phase is an encapsulating fluid that is immiscible with both the aqueous phase and the carrier fluid, and is less dense than both water and the carrier fluid. In this way a CLC is "triphasic", that is, it includes three mutually immiscible phases: a carrier fluid, an aqueous phase (sometimes called a sample) and an encapsulant. CLCs have proven to be robust and can be manipulated, e.g., moved from one location to another, added to, merged with other CLCs, split, etc. Encapsulation leaves CLCs essentially free of contamination. CLCs can also be formed down to very small sizes, and the small volumes involved allow for highly efficient use of potentially expensive reagents.

All these factors mean that CLCs are excellent venues for biological sample processing, for example, in PCR, dPCR, qPCR, TMA, bDNA, LCR, and nucleic acid library preparation.

While CLCs can be formed on the free surface of a large carrier liquid bath, triphasic arrangements of fluids can also be generated, stored, or otherwise located inside a small, self-contained vessel (or well). It is often necessary to remove the aqueous phase of a triphasic arrangement of fluids contained in a self-contained vessel or well for use in an assay or other process. For example, the triphasic arrangement of fluids in a vessel may include in the aqueous phase a predetermined quantity of a reagent to be removed from the vessel and added to a CLC at a predetermined stage of a particular protocol. Repeatably and reliably removing all of the aqueous phase from a triphasic arrangement of fluids in a vessel is important in maintaining the integrity of downstream processes using the components of the aqueous phase.

SUMMARY

Methods for removing a target fluid from a triphasic fluid arrangement as well as systems and methods for performing such methods are disclosed.

Aspects of the present disclosure include a method of moving a target fluid in a triphasic fluid arrangement from a vessel into a tube, the method comprising: (a) positioning an open distal end of a tube vertically along a sidewall of a vessel comprising a triphasic fluid arrangement, wherein the triphasic fluid arrangement comprises: a carrier fluid, a target fluid, and an encapsulating fluid, and wherein the open distal end of the tube is at least partially within the carrier fluid; and (b) drawing fluid into the tube through the open distal end, the drawn fluid comprising the target fluid and the encapsulating fluid.

In certain embodiments, the carrier fluid is denser than the target fluid and the target fluid is denser than the encapsulating fluid, wherein the three fluids are mutually immiscible.

In certain embodiments, the open distal end of the tube is entirely within the carrier fluid.

In certain embodiments, the sidewall of the vessel is constructed of a material such that an interface between the carrier fluid and the encapsulating fluid forms a meniscus in which the carrier fluid is convex and the encapsulating fluid is concave.

In certain embodiments, the vessel is cylindrical.

In certain embodiments, a portion of the vessel is conical.

In certain embodiments, a proximal end of the tube is operatively coupled to a pressure source, wherein drawing fluid into the tube through the open distal end comprises causing the pressure source to create a negative pressure at the distal end of the tube.

In certain embodiments, the target fluid is aqueous.

In certain embodiments, the target fluid comprises a biological sample and/or a reagent.

In certain embodiments, the density of the carrier fluid is from 1,300 to 2,000 kg/m$^3$.

In certain embodiments, the density of the target fluid is from 900 to 1,200 kg/m$^3$.

In certain embodiments, the density of the encapsulating fluid is from 700 to 990 kg/m$^3$.

In certain embodiments, the difference in density between the carrier fluid and the target fluid is from 50 to 2000 kg/m$^3$.

In certain embodiments, the difference in density between the target fluid and the encapsulating fluid is from 50 to 2000 kg/m$^3$.

In certain embodiments, the carrier fluid is a fluorocarbonated oil.

In certain embodiments, the encapsulating fluid is a silicone oil.

In certain embodiments, the method further comprises dispensing the target fluid in the tube into a desired receptacle.

In certain embodiments, the method further comprises moving a second target fluid in a second triphasic fluid arrangement from a second vessel into the tube.

In certain embodiments, the first target fluid is dispensed from the tube into a desired receptacle prior to moving the second target fluid into the tube.

In certain embodiments, the first target fluid and the second target fluid are present in the tube simultaneously.

In certain embodiments, a plurality of target fluids in corresponding triphasic fluid arrangements in vessels are moved into a plurality of corresponding tubes simultaneously.

In certain embodiments, the inner diameter of the tube is from 0.025 to 3.5 millimeters.

In certain embodiments, the tube is selected from the group consisting of: a capillary tube, a pipette tip, and a needle.

Aspects of the present disclosure include a triphasic fluid handling system configured to: (a) position an open distal end of a tube vertically along a sidewall of a vessel comprising a triphasic fluid arrangement, wherein the triphasic fluid arrangement comprises: a carrier fluid, a target fluid, and an encapsulating fluid, and wherein the open distal end of the tube is positioned at least partially within the carrier fluid; and (b) draw the target fluid and encapsulating fluid into the tube through the open distal end.

In certain embodiments, the carrier fluid is denser than the target fluid and the target fluid is denser than the encapsulating fluid, wherein the three fluids are mutually immiscible.

In certain embodiments, the system further comprises a pressure source operatively coupled to a proximal end of the tube and configured to create a negative pressure at the distal end of the tube to draw fluid into the tube through the open distal end.

In certain embodiments, the system is further configured to draw a second target fluid in a second triphasic fluid arrangement from a second vessel into the tube.

In certain embodiments, the system is further configured to move a plurality of target fluids in corresponding triphasic fluid arrangements in vessels into a plurality of corresponding tubes simultaneously.

In certain embodiments, the system is further configured to dispense the target fluid in the tube into a desired receptacle.

BRIEF DESCRIPTION OF THE DRAWINGS

Aspects of the disclosure may be best understood from the following detailed description when read in conjunction with the accompanying drawings.

Included in the drawings are the following figures.

DETAILED DESCRIPTION

Figure 1:
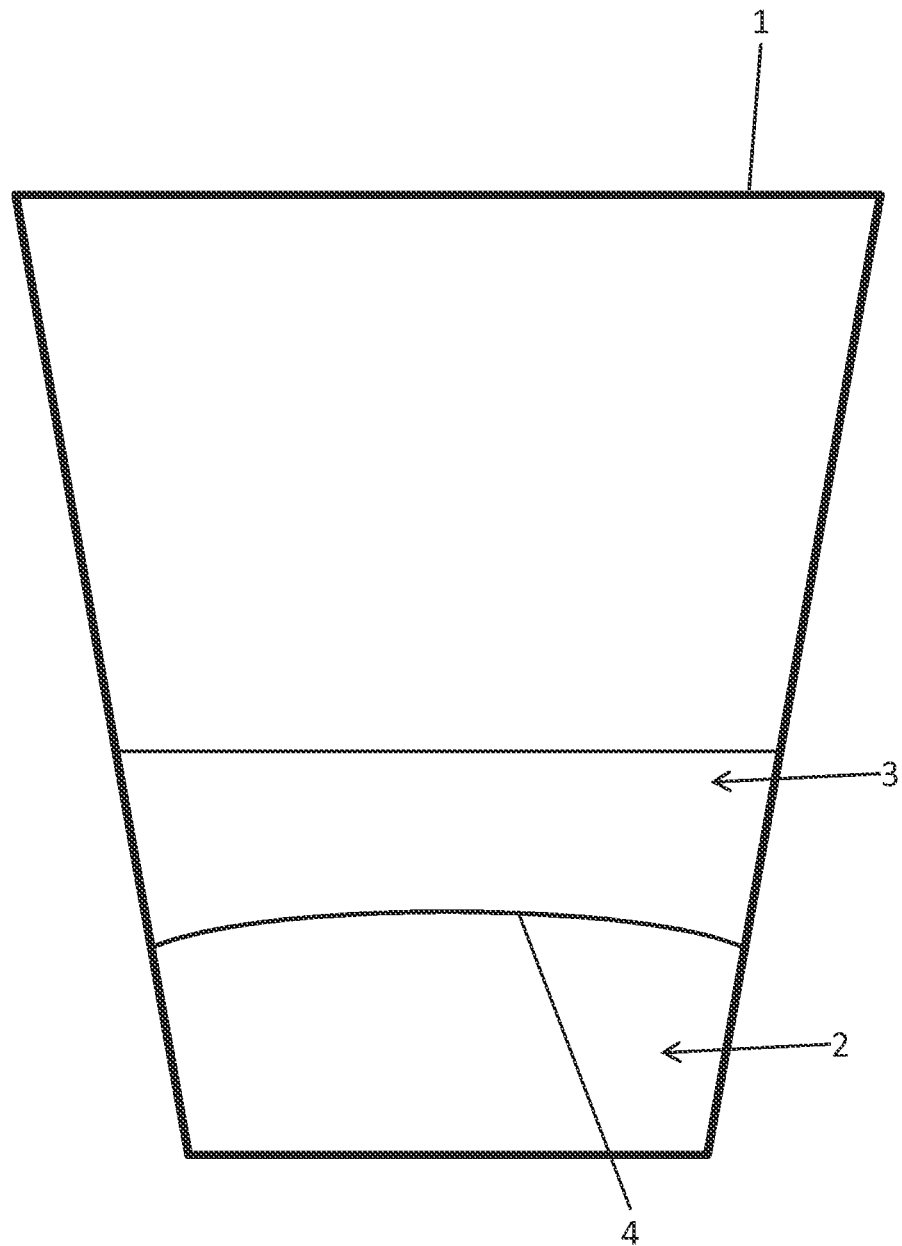
FIGS. 1-12 schematically show a vessel containing elements of a triphasic fluid arrangement, and target fluid being removed from the vessel according to aspects of the present disclosure.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, aspects of the present disclosure include methods of moving a target fluid in a triphasic fluid arrangement from a vessel into a tube and systems and devices for performing such methods.

As used herein, a triphasic fluid arrangement is a combination of at least three substantially mutually immiscible fluids having three different densities. The first fluid is a carrier fluid which is the densest of the three substantially mutually immiscible fluids; the second fluid is an encapsulating fluid which is the least dense of the substantially mutually immiscible fluids; and the third fluid is a target fluid (sometimes referred to as a "sample") which has a density that is less than the first fluid and greater than the second fluid. Thus, in a triphasic fluid arrangement, the target fluid is encased (or encapsulated) between the carrier fluid and the encapsulating fluid. In certain embodiments, the target fluid is an aqueous fluid, where in some embodiments the aqueous fluid contains a biological sample, reagent, buffer, or other prescribed element of a biological assay or biochemical protocol. Examples of components that can be present in the aqueous fluid include, but are not limited to: cells, nucleic acids, proteins, enzymes, biological sample (e.g., blood, saliva, etc.), buffers, salts, organic material, and any combination thereof.

In certain embodiments, the density of the carrier fluid is from 1,300 to 2,000 kg/m$^3$, the density of the target fluid is from 900 to 1,200 kg/m$^3$, and the density of the encapsulating fluid is from 700 to 990 kg/m$^3$. The difference in density between the carrier fluid and the target fluid or between the target fluid and the encapsulating fluid is from 50 to 2000 kg/m$^3$. In general, the difference in density between the three substantially mutually immiscible fluids should be sufficient to prevent substantial intermixing between any two of them under the conditions in which they are to be stored and/or used in any downstream process or analytical assay. Additional details regarding carrier, encapsulating and target fluids may be found in U.S. Pat. Nos. 8,465,707; 9,080,208 and 9,777,269; and Published PCT Application Nos: WO2014/083435; WO2014/188281;

WO2014/207577; WO2015/075563; WO2015/075560; the disclosures of which applications are herein incorporated by reference.

In certain embodiments, carrier fluid and/or the encapsulating fluid is an oil. For example, in certain embodiments, the carrier and/or the encapsulating fluid can be a silicone oil, a perfluorocarbon oil, or a perfluoropolyether oil. Thus, in certain embodiments, the carrier fluid is selected from fluorocarbonated oils. In certain embodiments, the encapsulating fluid is selected from a silicone oils.

In embodiments in which the target fluid is an aqueous fluid, for example, a biological sample or an aqueous reagent, an example of a triphasic fluid arrangement includes one in which the carrier (first) fluid is Fluorinert FC-40 (fluorocarbonated oil) having a density of approximately 1,900 kg/m$^3$, the second fluid is a phenylmethylpolvsiloxane (silicone oil) having a density of approximately 920 kg/m$^3$, and the target fluid (sample) is an aqueous-based solution of biological components with a density of approximately 1000 kg/m$^3$.

In certain embodiments, the volume of the target fluid (sample) in the triphasic fluid arrangement is from about 10 nanoliters (nL) to about 20 microliters (μL). As such, in certain embodiments, the volume of the sample is about 10 nL, about 20 nL, about 30 nL, about 40 nL, about SO nL, about 60 nL, about 70 nL, about 80 nL, about 90 nL, about 100 nL, about 200 nL, about 300 nL, about 400 nL, about 500 nL, about 600 nL, about 700 nL, about 800 nL, about 900 nL, 1 μL, about 2 μL, about 3 μL, about 4 μL, about 5 μL, about 6 μL, about 7 μL, about 8 μL, about 9 μL, about 10 μL, about 11 μL, about 12 μL, about 13 μL, about 14 μL, about 15 μL, about 16 μL, about 17 μL, about 18 μL, about 19 μL, or about 20 μL.

The volume of the carrier and encapsulating fluid in a triphasic fluid arrangement should be sufficient to generate a composition in which the target fluid can be fully encapsulated between these fluids when present in a desired vessel. By fully encapsulated is meant that the target fluid is in direct contact with only the encapsulating fluid and/or the carrier fluid. Thus, the target fluid is not in contact with either the bottom of the vessel (generally below the carrier fluid) or to the ambient environment (generally above the encapsulating fluid). The amount of fluid is thus dependent not only on the volume of the target fluid, but also on the interior dimensions of the vessel. While the volume of carrier and encapsulating fluid can vary greatly, in certain embodiments, the volume of the carrier fluid or the encapsulating fluid in the triphasic fluid arrangement is from about 1 μL to about 100 μL. As such, in certain embodiments, the volume of the carrier fluid or the encapsulating is about 1 μL, about 2 μL, about 3 μL, about 4 μL, about 5 μL, about 6 μL, about 7 μL, about 8 μL, about 9 μL, about 10 μL, about 11 μL, about 12 μL, about 13 μL, about 14 μL, about 15 μL, about 16 μL, about 17 μL, about 18 μL, about 19 μL, about 20 μL, about 25 μL, about 30 μL, about 35 μL, about 40 μL, about 45 μL, about 50 μL, about 55 μL, about 60 μL, about 65 μL, about 70 μL, about 75 μL, about 80 μL, about 85 μL, about 90 μL, about 95 μL, or about 100 μL.

The vessel in which the triphasic fluid arrangement is formed can be of any convenient shape or made from any convenient material that allows for the maintenance of the triphasic fluid arrangement and insertion of a tube for harvesting the target fluid therein (as described in further detail herein). In certain embodiments, the sidewall of the vessel is constructed of a material such that an interface between the carrier fluid and the encapsulating fluid forms a meniscus in which the carrier fluid is convex and the encapsulating fluid is concave. Conversely, in some embodiments the sidewall of the vessel is constructed of a material such that an interface between the carrier fluid and the encapsulating fluid forms a meniscus in which the carrier fluid concave is and the encapsulating fluid is convex. In certain embodiments, the sidewall of the vessel is constructed of a material such that an interface between the carrier fluid and the encapsulating fluid forms a planar interface (without an obvious concave/convex interface). The sidewall can have a shape that is completely or partially cylindrical, conical, frustoconical, rectangular prism, or any other shape. For example, a vessel having a sidewall that is conical at the open end (top) and cylindrical at the closed end (bottom) is partially conical. This shape is commonly seen in microfuge tubes, e.g., Eppendorf Tubes®.

In certain embodiments, the vessels in which triphasic fluid arrangements are present include standard commercially available individual vessels or multiplexed vessels (e.g., strips of wells or multiwell plates) that are routinely used in biochemical analyses.

In certain embodiments, a method of moving a target fluid in a triphasic fluid arrangement from a vessel into a tube includes: (a) positioning an open distal end of a tube vertically along a sidewall of a vessel comprising a triphasic fluid arrangement (as described above) such that the open distal end of the tube is at least partially within the carrier fluid; and (b) drawing fluid into the tube through the open distal end, where the drawn fluid contains the target fluid (i.e., the target fluid is drawn into the tube). In certain embodiments, the drawn fluid includes substantially all of the target fluid and substantially all of the encapsulating fluid. In some embodiments, the tube is positioned in step (a) such that the open distal end is entirely within the carrier fluid of the triphasic fluid arrangement.

In general, the dimensions of the tube employed are based on the desires of the user and will be selected such that it can be positioned in the vessel and will effectively draw fluid from the vessel. In certain embodiments, the tube has an internal diameter of from about 10 microns (μ) to about 10 millimeters (mm) in diameter, e.g., from about 25μ to about 3.5 mm, and including about 10μ, about 20μ, about 30μ, about 40μ, about 50μ, about 60μ, about 70μ, about 80μ, about 90μ, about 100μ, about 150μ, about 200μ, about 250μ, about 500μ, about 1 mm, about 2 mm, about 3 mm, about 4 mm, 5 mm, about 6 mm, about 7 mm, about 8 mm, 9 mm, or about 10 mm. In certain embodiments, the internal diameter of the tube is variable along the length of the tube, e.g., from the open distal end (the bottom) of the tube to the proximal end (the top) of the tube. In certain embodiments, the tube has a wall thickness of at least about 10 microns or more.

In certain embodiments, the tube is made from a glass, a polymer, a ceramic, a metal, or a combination thereof. In certain embodiments, the tube is selected from the group consisting of: a pipette tip, a capillary, and a needle. In certain embodiments, the tube includes an internal or external hydrophobic surface. In certain embodiments, the tube is disposable. In certain embodiments, the tube is reusable.

In certain embodiments, the tube has a proximal (top) end that is operatively coupled to a pressure source, or pump. Drawing fluid into the tube through the open distal end can thus include causing the pressure source to create a negative pressure at the distal end of the tube. In certain embodiments the pump is selected form a vacuum pump and a pipette bulb.

FIGS. 1 to 12 are described in detail below to illustrate specific embodiments of aspects of the present disclosure.

FIG. 1 shows a vessel 1 containing a carrier fluid 2 and an encapsulating fluid 3. The carrier fluid 2 and encapsulating fluid 3 are immiscible, forming separate domains with a well-defined boundary meniscus 4. The carrier fluid 2 is denser than the encapsulating fluid 3, and therefore sits beneath the encapsulating fluid. In this example, the carrier fluid 2 and the encapsulating fluid 3 form a meniscus 4 that bulges upward, so that the carrier fluid 2 has a convex upper surface and the encapsulating fluid has a concave lower surface. The shape and orientation of the meniscus 4 will depend on the properties of the interior of the vessel 1 relative to the carrier fluid 2 and the encapsulating fluid 3. Embodiments in which a meniscus between the carrier and encapsulating fluids bulges in the opposite direction, or is entirely flat (planar), are also contemplated (as described above).

Figure 2:
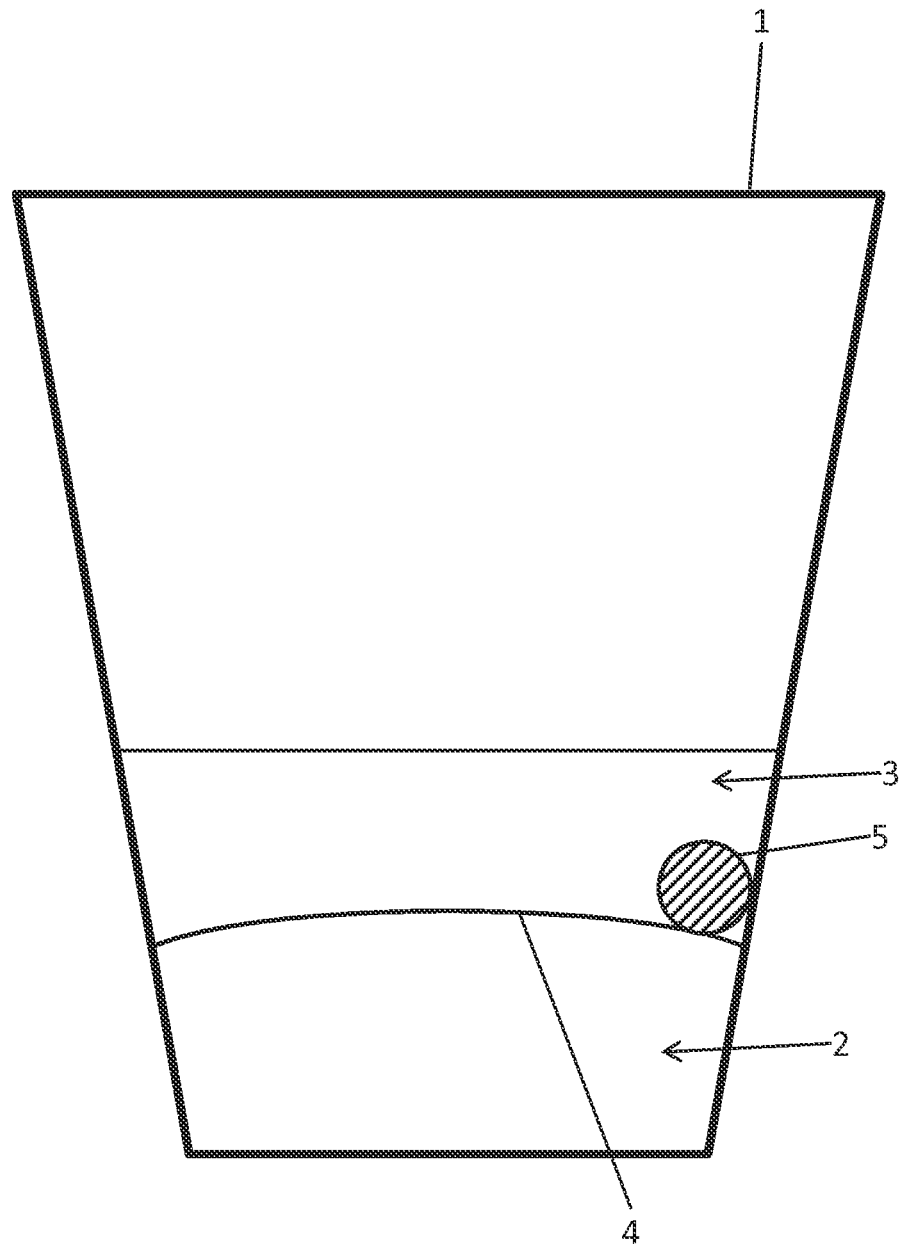

FIG. 2 shows the same vessel 1 further including a target fluid 5. The target fluid 5 is immiscible in both the carrier fluid 2 and the encapsulating fluid 3. The target fluid 5 is denser than the encapsulating fluid 3, but less dense than the carrier fluid 2. The target fluid 5 can be introduced into the vessel 1 as a bare drop of target fluid or encapsulated in encapsulating fluid. The shape of the meniscus 4 will tend to cause the target fluid 5 to settle at the side of the vessel 1.

Figure 3:
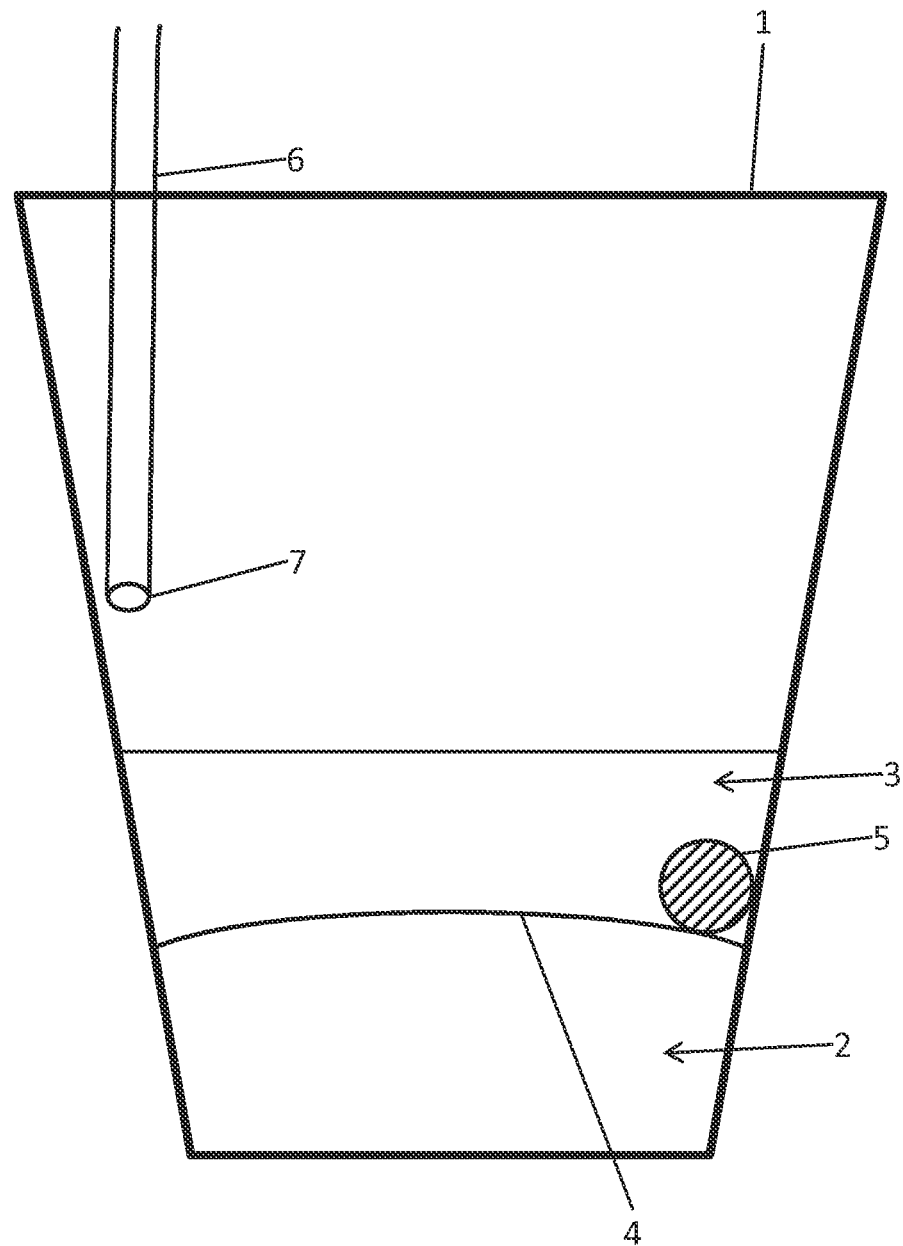

FIG. 3 shows the same vessel 1 including the three fluids, and also shows a tube 6 being advanced into the vessel 1. The tube has an open distal end 7. The proximal end of the tube is not shown, but can be attached to a pressure source capable of producing a negative pressure in order to draw fluids into the distal end 7 of the tube 6. The tube 6 is advanced near the side wall of the vessel 1. In this case the side wall is sloped, the vessel 1 being frustoconical, shown as an isosceles trapezoid in cross-section in the figures.

Figure 4:
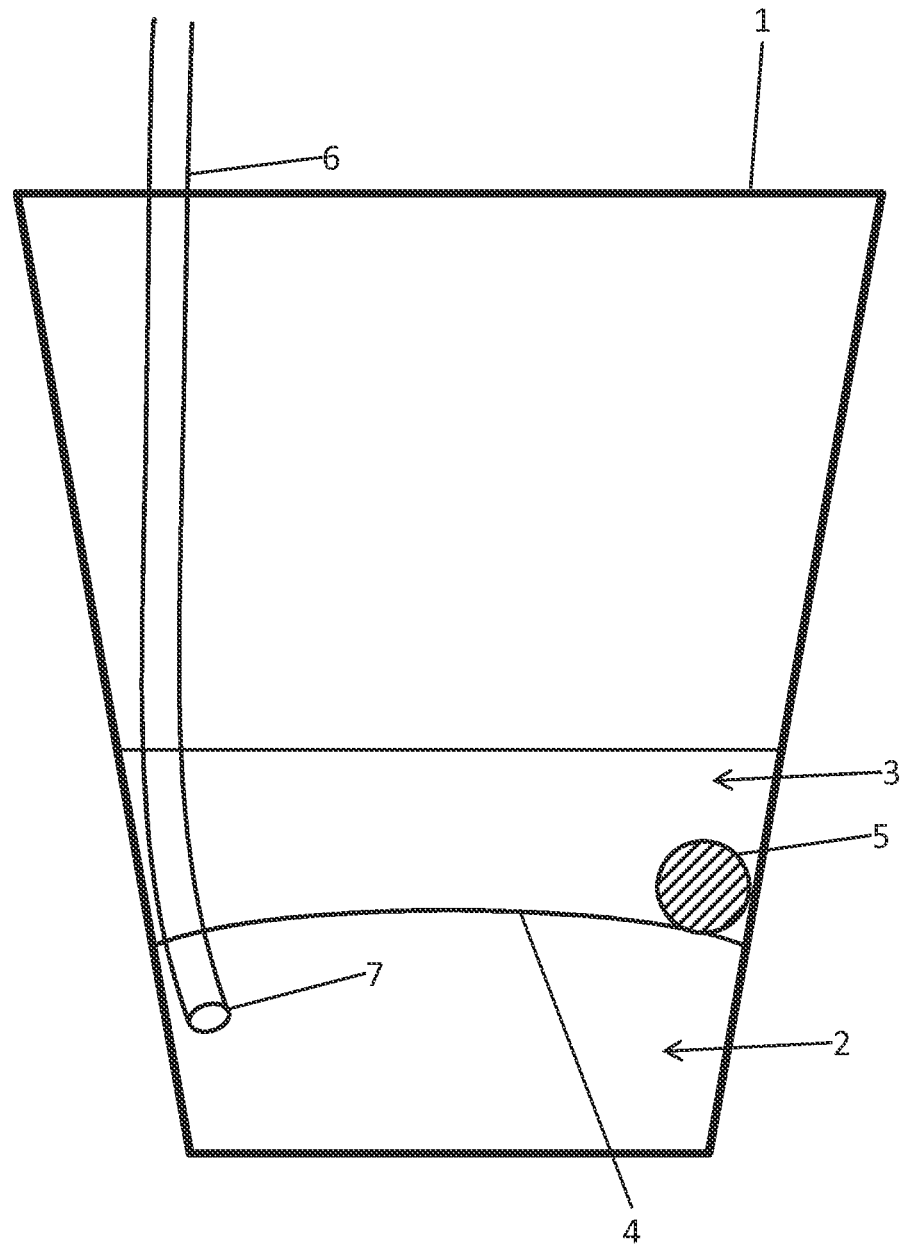

FIG. 4 shows the same vessel 1 and tube 6, the tube 6 now having been advanced so that the distal end 7 has contacted the side wall and slid downward along the side wall until the distal end 7 is entirely submerged in the carrier fluid 2.

Figure 5:
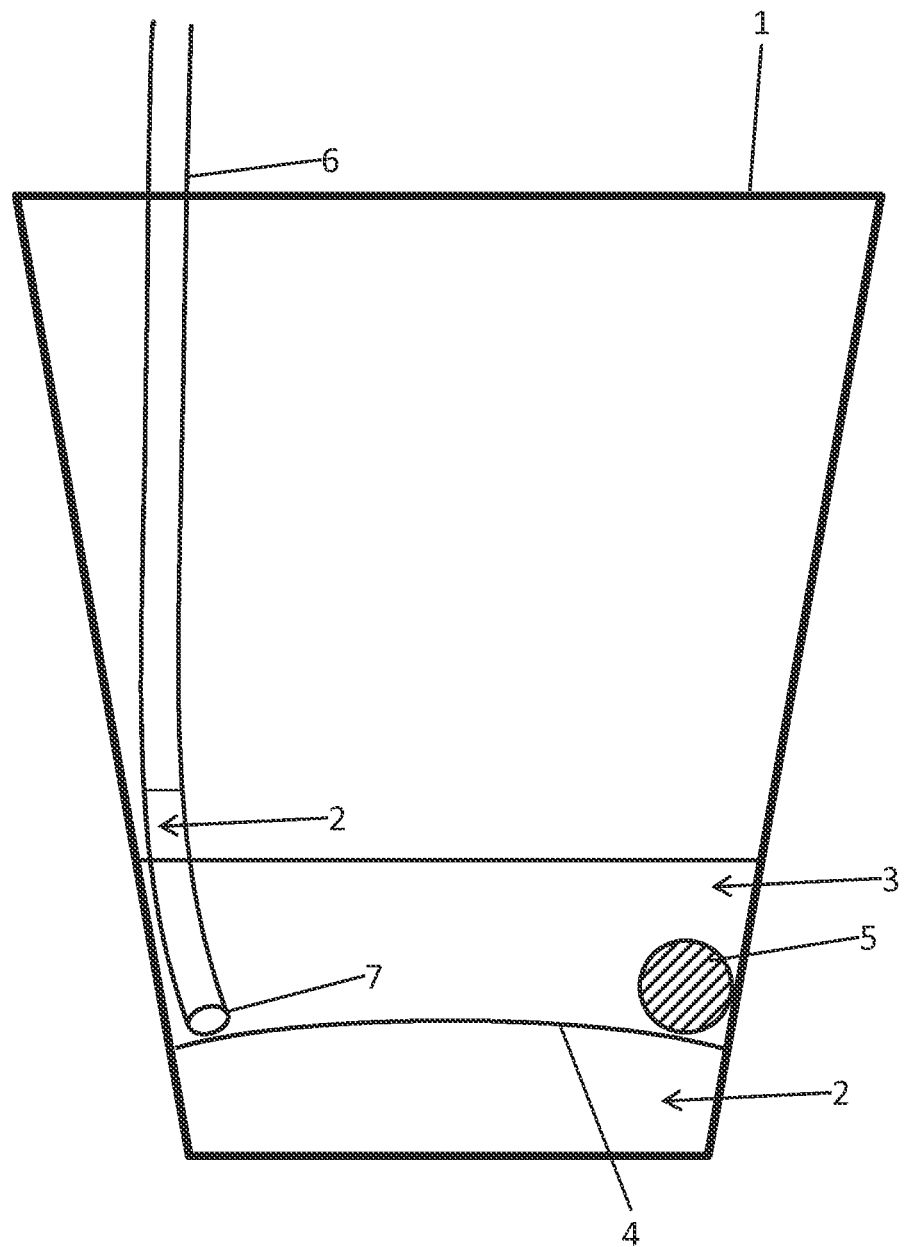

FIG. 5 shows the same vessel 1 and tube 6 after the tube 6 has been advanced, and after the pressure source has been activated to provide a negative pressure and aspirate fluid. When the pressure source is first activate, the first fluid to be aspirated upward through the tube 6 is the carrier fluid 2. As shown in FIG. 5, carrier fluid 2 is aspirated into the tube 6 until the distal end 7 is roughly coincident with the meniscus. At that point, encapsulating fluid 3 may begin to be aspirated. In the instance shown in the figures, the target fluid 5 is located across the vessel 1 from the tube 6, but in fact the positions of the target fluid 5 and the tube 6 will be uncorrelated. The target fluid 5 could just as easily be at or near the distal end 7 of the tube 6. If so, the target fluid 5 will be aspirated after little or no encapsulating fluid 3 has been aspirated. But even if the target fluid 5 is at the farthest possible point from the distal end 7, the target fluid 5 will eventually be drawn into the distal end 7. As more encapsulating fluid 3 is aspirated, eventually surface tension will cause the remaining encapsulating fluid to "neck" or "break" near the target fluid 5.

Figure 6:
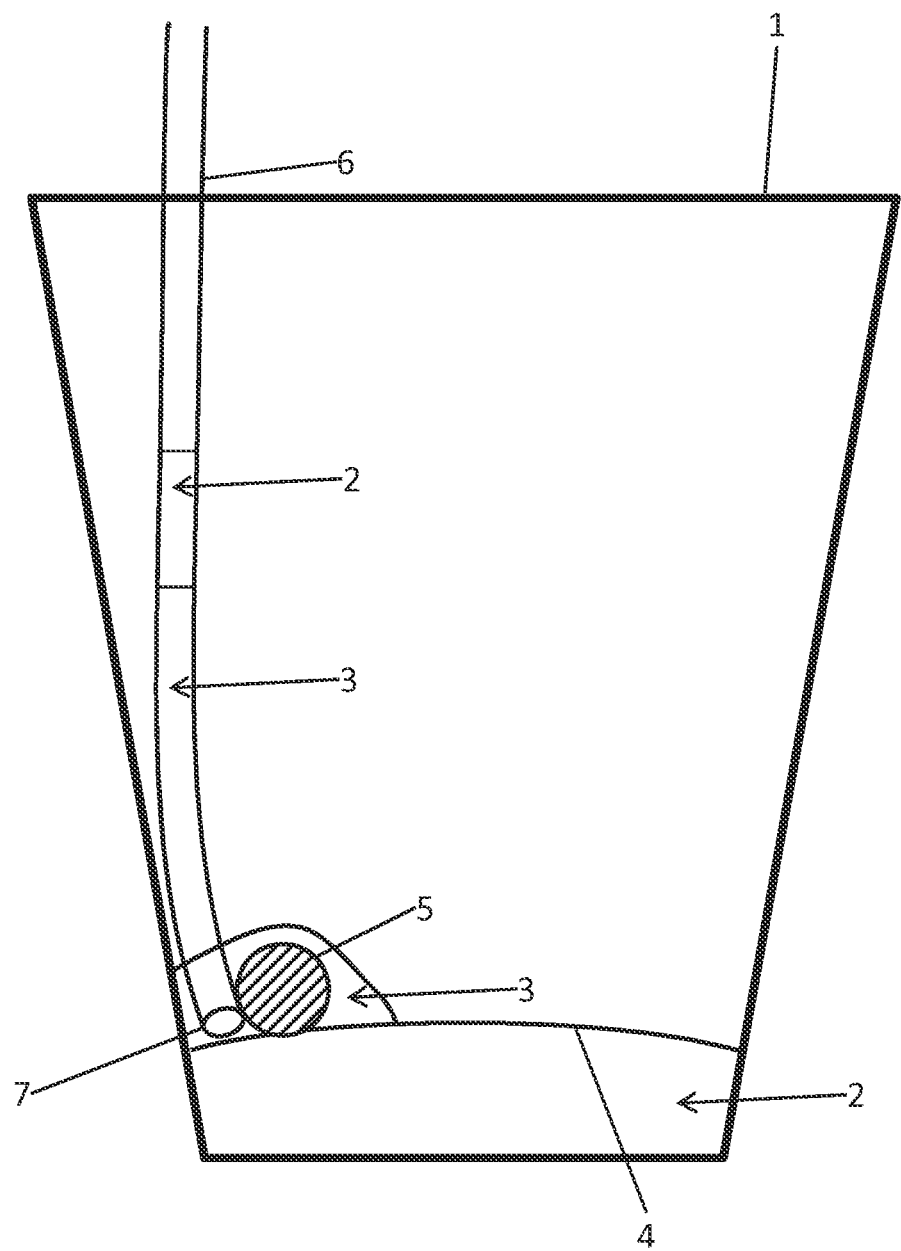

FIG. 6 shows the same vessel 1 and tube 6 after most of the encapsulating fluid 3 has been aspirated and is present in the tube 6. In this case, because the target fluid 5 was situated far from the distal end 7 of the tube 6, most of the encapsulating fluid 3 is aspirated before the target fluid 5 is aspirated.

Figure 7:
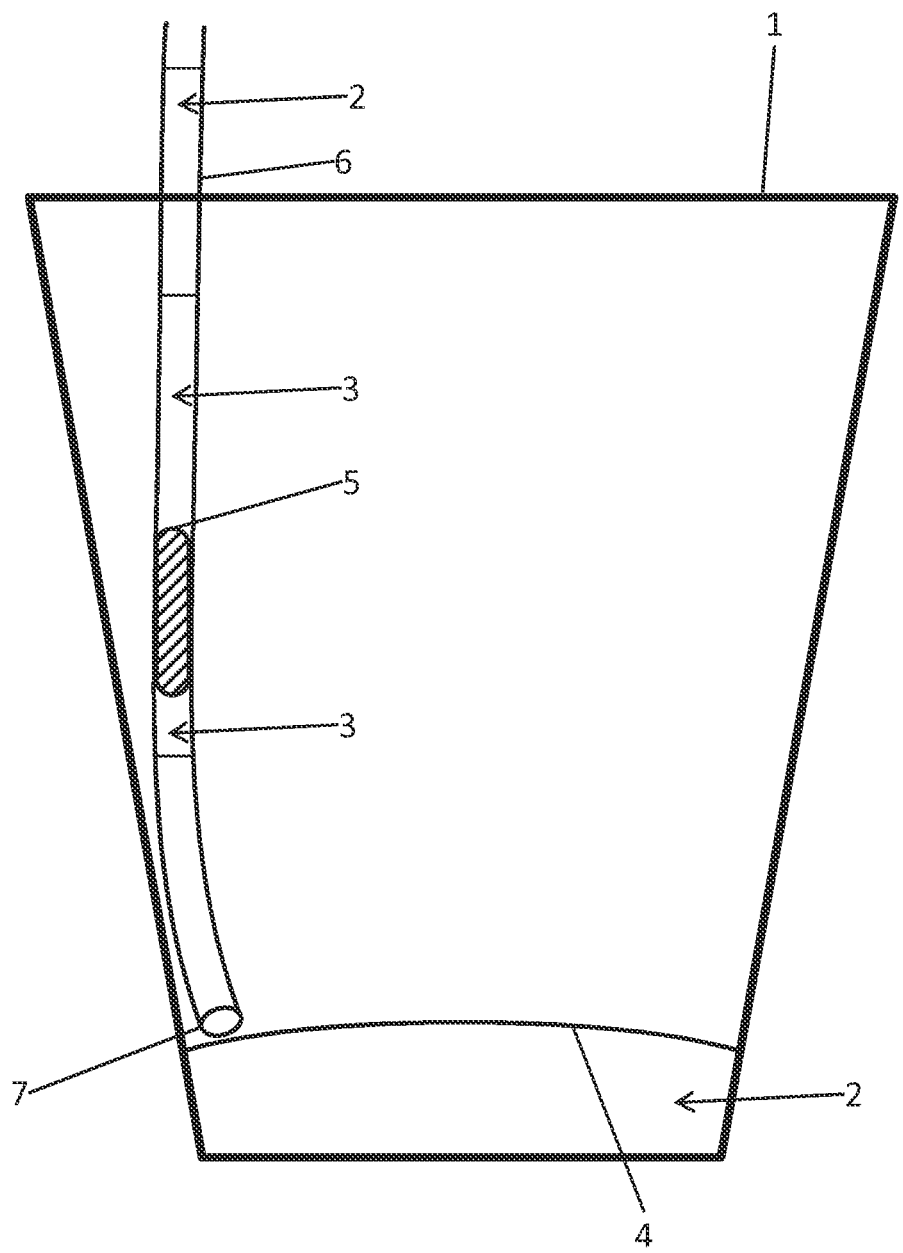

FIG. 7 shows the same vessel 1 and tube 6 after the target fluid 5 and all of the encapsulating fluid 3 has been aspirated. At this point, aspiration can stop, since the tube 6 is no longer in contact with any of the three fluids, the tube 6 can be removed from the vessel 1 and repositioned at a location where the target fluid 5 is to be dispensed.

FIGS. 8-12 show the top view of the aspiration process described in the previous FIGS.

Figure 8:
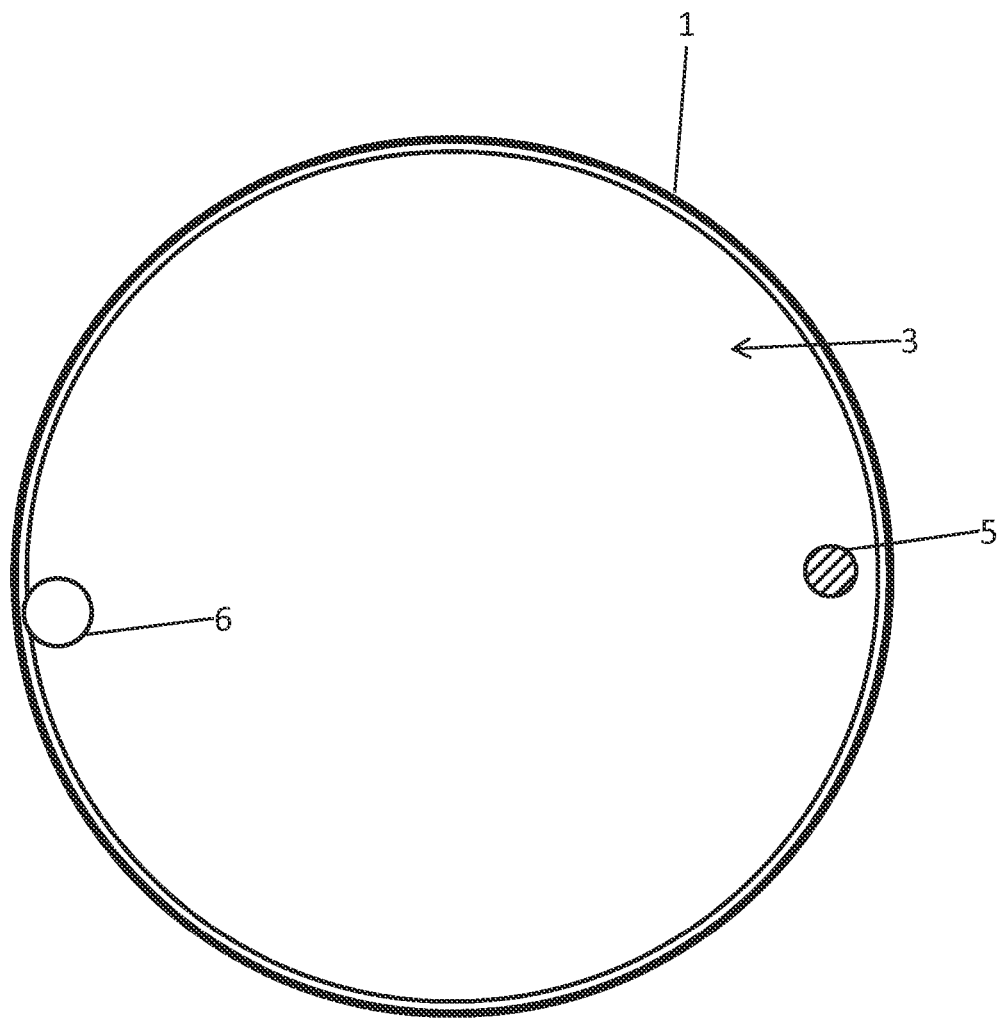

In FIG. 8, the vessel 1 is viewed from above, with the encapsulating fluid 3 entirely covering the carrier fluid (not visible), similar to the situation shown in profile in FIGS. 4 and 5. For clarity, the target fluid 5 is shown, even though through the entire process it is still entirely covered by the encapsulating fluid 3.

Figure 9:
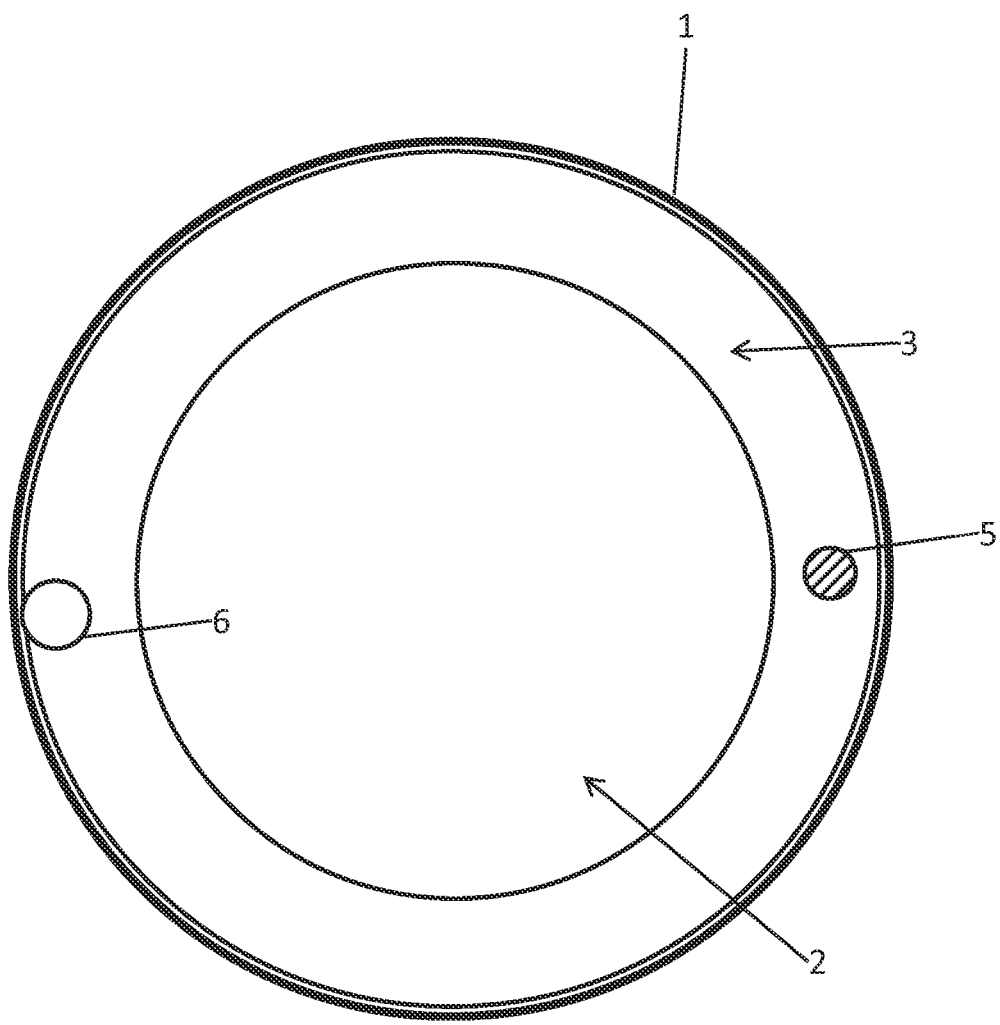

In FIG. 9, more of the encapsulating fluid 3 has been aspirated leaving only a ring around the lowest part of the meniscus.

Figure 10:
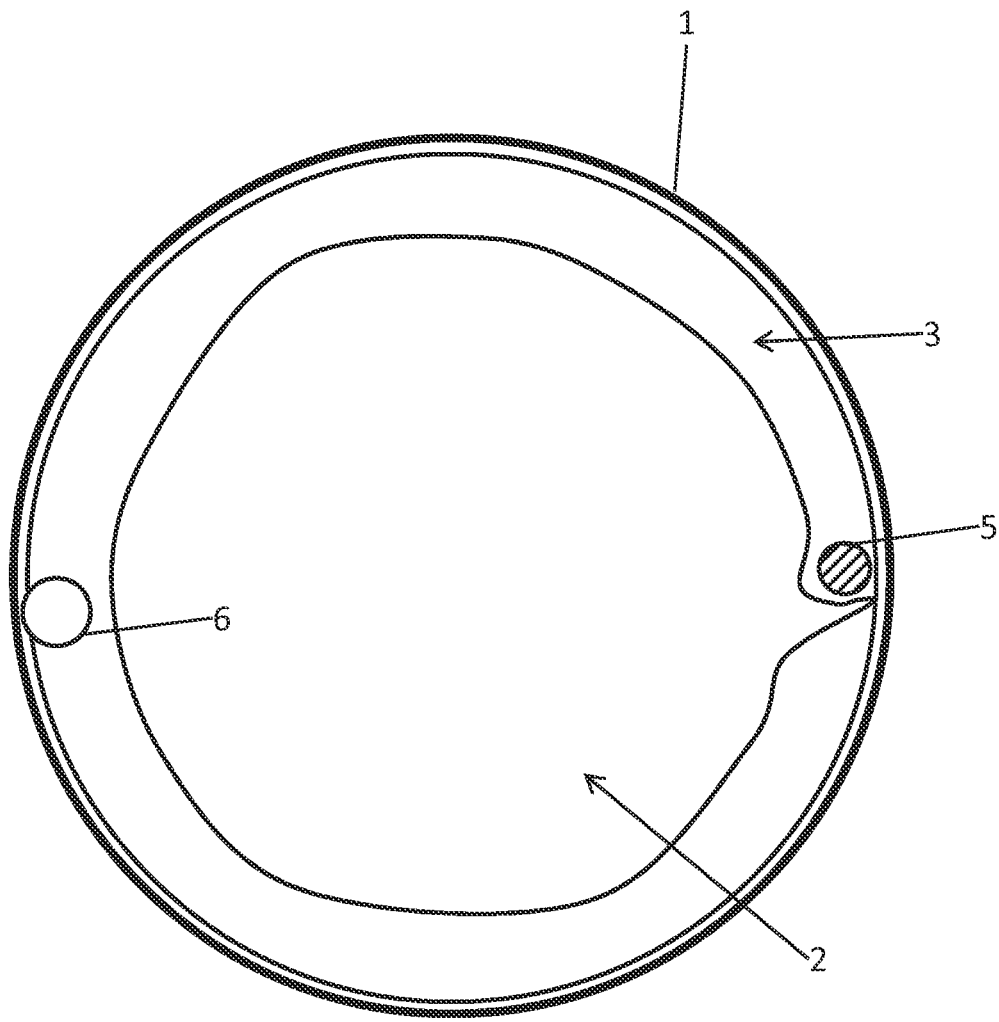

FIG. 10 shows the encapsulating fluid 3 necking down and breaking near the target fluid 5 a more encapsulating fluid is aspirated.

Figure 11:
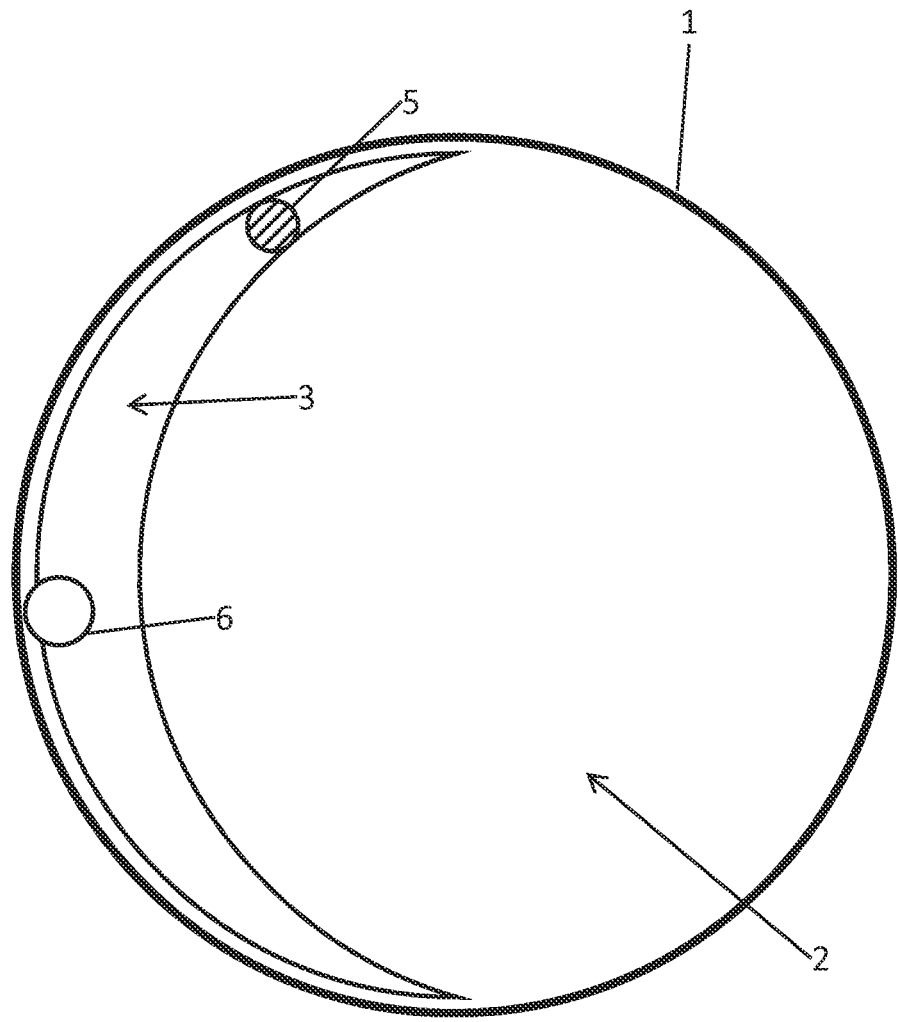

FIG. 11 shows the encapsulating fluid 3 having fully broken, no longer forming a ring at all, and carrying the target fluid 5 along toward the tube 6 as encapsulating fluid 3 continues to be drawn in.

Figure 12:
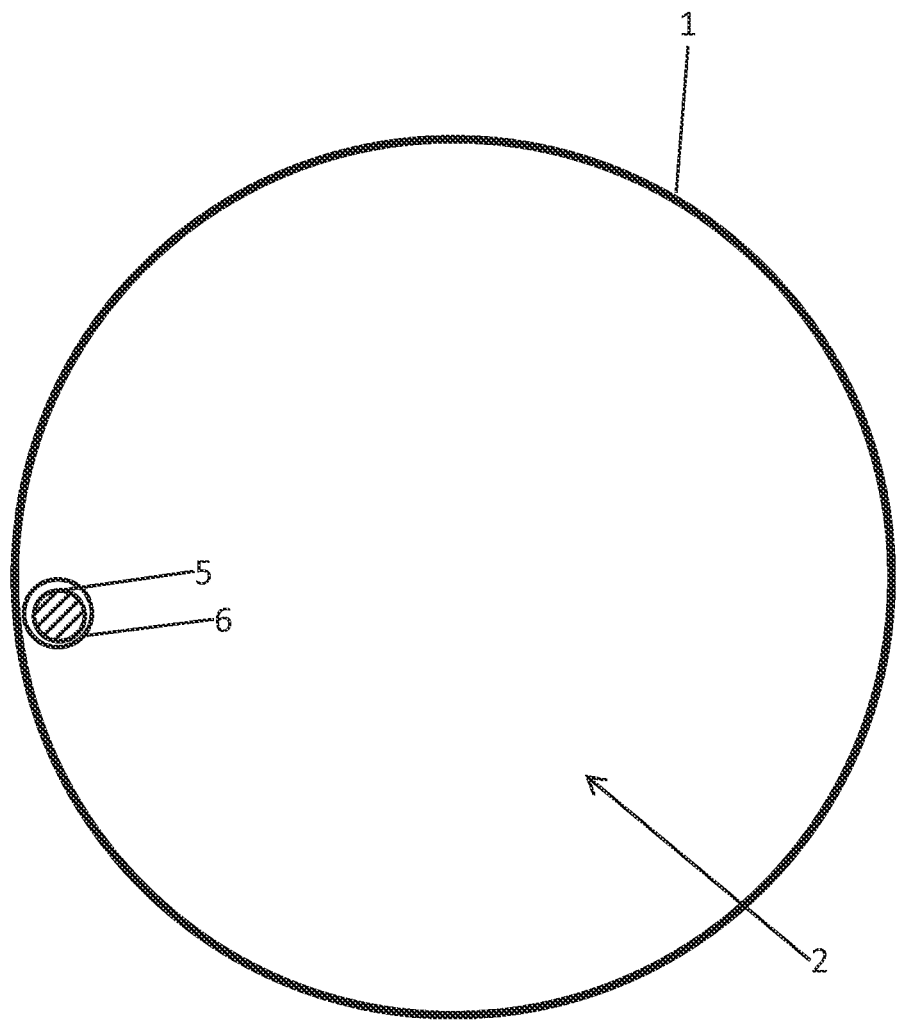

FIG. 12 finally shows the target fluid 5 having been fully aspirated and drawn into the tube 6.

The result of the process shown, in which the distal end 7 is positioned below the initial position of the meniscus 4, is that the target fluid 5 is consistently aspirated in its entirety, typically surrounded by at least some encapsulating fluid 3 inside the tube 6. As described below, this arrangement of fluids in the tube is useful for later dispensing of the target fluid, e.g. into a receptacle containing a CLC.

In certain embodiments, the method further includes dispensing the target fluid in the tube into a desired receptacle. This can be achieved by positioning the open distal end of the tube containing the target fluid in or over a desired receptacle and dispensing the target fluid therein. As noted above, the drawn fluid can contain encapsulating fluid in addition to the target fluid, and thus some encapsulating fluid can be dispensed along with the target fluid into the desired receptacle. In certain embodiments, some carrier fluid might also be present in the drawn fluid in the tube and will also be dispensed along with the target fluid and the encapsulating fluid into the desired receptacle. Any convenient manner for dispensing the drawn fluid can be used, including gravity, suction, capillary action, etc. Where the tube is operably connected to a pressure source (or pump), dispensing the drawn fluid in the tube can be achieved by applying positive pressure by the pressure source to the proximal end of the tube.

As indicated above, the receptacle into which the drawn fluid in the tube is dispensed can contain a sample, e.g., a CLC containing a sample, with which the target fluid is to be combined. Thus, the receptacle can contain a CLC-based biochemical assay reaction or sample, e.g., as described in U.S. Pat. No. 8,465,707, hereby incorporated by reference herein in its entirety.

In certain embodiments, the method includes drawing more than one target fluid into the tube. For example, the tube may be moved from a first vessel from which a first target fluid from a first triphasic fluid arrangement was drawn to a second vessel containing a second triphasic fluid arrangement containing a second target fluid and performing the positioning and drawing steps ad recited above to draw the second target fluid into the tube. In certain embodiments, the first target fluid remains in the tube while the second target fluid is drawn into the tube, whereas in other embodiments, the first target fluid is dispensed from the tube into a desired receptacle prior to drawing the second target fluid into the tube. Thus, in the former embodiment, the first target fluid and the second target fluid are present in the tube simultaneously.

In certain embodiments, a plurality of target fluids in corresponding triphasic fluid arrangements in vessels are moved into a plurality of corresponding tubes. For example, where the vessels are present in a multiplex configuration (e.g., the wells of a standard microwell plate), the open distal end of a plurality of tubes in a configuration that matches the spacing of some or all of the plurality of vessels in the multiplex configuration are positioned in plurality vessels to draw the corresponding target fluids into the tubes. In other embodiments, the open distal end of each of the plurality of tubes, or each subset of a plurality of tubes, is positioned independently to draw the target fluid into the tubes.

As with the individual tube described above, in certain embodiments, the proximal end of the plurality of tubes are operably coupled to one or more a pressure sources (or pumps), where in certain embodiments, the pressure source creates a negative pressure at the distal end of the plurality of tubes to draw fluid therein. In addition, the plurality of target fluids in the plurality of corresponding tubes can be dispensed at a desired location or in one or more desired receptacles. In such embodiments, each of the plurality of target fluids can be dispensed at a different corresponding desired location/receptacle or, in certain embodiments, multiple different target fluids can be dispensed in the same location/receptacle. Moreover, the plurality of target fluids may be dispensed from the plurality of different tubes at different times.

For example, 10 different target fluids can be drawn into 10 different tubes simultaneously. Target fluids 1 to 5 can be dispensed into a first receptacle (or reaction vessel) and target fluids 6 to 10 can be dispensed into a second receptacle such that target fluids 1 and 6 are dispensed into their corresponding receptacles first, target fluids 2 and 7 are dispensed second, target fluids 3 and 8 are dispensed third, etc. The time-wise addition of the reagents would allow for a specific biochemical process to be carried out in each receptacle, e.g., the deposition of a nucleic acid sample (target fluids 1 and 6), the addition a restriction enzyme to digest the nucleic acids in the sample (target fluids 2 and 7), the addition of nucleic acid adapters (target fluids 3 and 8), the addition of a ligase to attach the adapters to the digested nucleic acids (target fluids 4 and 9), and the addition of reagents for adapter-mediated amplification (target fluids 5 and 10).

The desired dispensing location/receptacle is generally determined by the desires of the user.

The present disclosure provides systems and devices configured to perform the methods described herein (e.g., as summarized and described in detail above). Thus, aspects of the present disclosure include a triphasic fluid handling system or device configured to: (a) position an open distal end of a tube vertically along a sidewall of a vessel comprising a triphasic fluid arrangement where the open distal end of the tube is positioned at least partially within the carrier fluid of the triphasic fluid arrangement; and (b) draw the target fluid and encapsulating fluid into the tube through the open distal end.

In certain embodiments, the system further comprises a pressure source operatively coupled to a proximal end of the tube and configured to create a negative pressure at the distal end of the tube to draw fluid into the tube through the open distal end.

In certain embodiments, the system is further configured to draw a second target fluid in a second triphasic fluid arrangement from a second vessel into the tube.

In certain embodiments, the system is further configured to move a plurality of target fluids in corresponding triphasic fluid arrangements in vessels into a plurality of corresponding tubes simultaneously or sequentially.

In certain embodiments, the system is further configured to dispense the target fluid (or plurality of target fluids) in the tube (or plurality of tubes) into a desired receptacle (or a plurality of receptacles). Additional details regarding systems that may be configured to perform the fluid manipulation methods described herein, and therefore include the fluid handling systems described herein; include those described in U.S. Pat. Nos. 8,465,707; 9,080,208 and 9,777,269; and Published PCT Application Nos: WO2014/083435; WO2014/188281; WO2014/207577; WO2015/075563; WO2015/075560; the disclosures of which applications are herein incorporated by reference.

The methods and systems described herein find use in a variety of different applications. Applications in which the methods and systems find use include CLC mediated protocols, including but not limited to those described in U.S. Pat. Nos. 8,465,707; 9,080,208 and 9,777,269; and Published PCT Application Nos: WO2014/083435; WO2014/188281; WO2014/207577; WO2015/075563; WO2015/075560; the disclosures of which applications are herein incorporated by reference.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A method of moving a target fluid in a triphasic fluid arrangement from a vessel into a tube, the method comprising:
   (a) positioning an open distal end of a tube vertically along a sidewall of a vessel comprising a triphasic fluid arrangement, wherein the triphasic fluid arrangement comprises: a carrier fluid, a target fluid, and an encapsulating fluid, and wherein the open distal end of the tube is at least partially within the carrier fluid; and (b) drawing fluid into the tube through the open distal end, the drawn fluid comprising the target fluid and the encapsulating fluid.

2. The method of claim 1, wherein the carrier fluid is denser than the target fluid and the target fluid is denser than the encapsulating fluid, wherein the three fluids are mutually immiscible.

3. The method of claim 1, wherein the open distal end of the tube is entirely within the carrier fluid.

4. The method of claim 1, wherein the sidewall of the vessel is constructed of a material such that an interface between the carrier fluid and the encapsulating fluid forms a meniscus in which the carrier fluid is convex and the encapsulating fluid is concave.

5. The method of claim 1, wherein the vessel is cylindrical.

6. The method of claim 1, wherein a portion of the vessel is conical.

7. The method of claim 1, wherein a proximal end of the tube is operatively coupled to a pressure source, wherein drawing fluid into the tube through the open distal end comprises causing the pressure source to create a negative pressure at the distal end of the tube.

8. The method of claim 1, wherein the target fluid is aqueous.

9. The method of claim 8, wherein the target fluid comprises a biological sample and/or a reagent.

10. The method of claim 1, further comprising dispensing the target fluid in the tube into a desired receptacle.

11. The method of claim 1, further comprising moving a second target fluid in a second triphasic fluid arrangement from a second vessel into the tube.

12. The method of claim 11, wherein the first target fluid is dispensed from the tube into a desired receptacle prior to moving the second target fluid into the tube.

13. The method of claim 11, wherein the first target fluid and the second target fluid are present in the tube simultaneously.

14. The method of claim 1, wherein a plurality of target fluids in corresponding triphasic fluid arrangements in vessels are moved into a plurality of corresponding tubes simultaneously.

15. The method of claim 1, wherein the inner diameter of the tube is from 0.025 to 3.5 millimeters.

16. The method of claim 1, wherein the tube is selected from the group consisting of: a capillary tube, a pipette tip, and a needle.

17. The method of claim 1, wherein the target fluid is encapsulated by the encapsulating fluid.

* * * * *